United States Patent [19]
Hirako et al.

[11] Patent Number: 5,158,889
[45] Date of Patent: Oct. 27, 1992

[54] BIOLOGICAL CELL SORTER

[75] Inventors: Shin-ichi Hirako, Nagaokakyo; Yoshihiro Nakatsuji, Uji, both of Japan

[73] Assignee: Omron Corporation, Kyoto, Japan

[21] Appl. No.: 452,749

[22] Filed: Dec. 21, 1989

[30] Foreign Application Priority Data

Dec. 22, 1988 [JP] Japan .................. 63-324035

[51] Int. Cl.⁵ .............................. C12M 1/36
[52] U.S. Cl. ............................ 435/289; 435/287; 435/291; 435/311; 435/808; 250/461.2; 250/492.1
[58] Field of Search ............. 435/289, 291, 808, 2, 435/173, 287, 311; 436/63, 175, 805, 825, 172; 250/459.1, 461.2, 492.1; 422/20-24; 356/39

[56] References Cited

U.S. PATENT DOCUMENTS

| | | | |
|---|---|---|---|
| 3,817,703 | 6/1974 | Atwood | 422/22 |
| 4,395,397 | 7/1983 | Shapiro | 424/101 |
| 4,500,641 | 2/1985 | van den Engh et al. | 435/291 |
| 4,624,915 | 11/1986 | Schindler et al. | 435/4 |
| 4,629,684 | 12/1986 | Schindler et al. | 435/4 |

*Primary Examiner*—Robert J. Warden
*Assistant Examiner*—William H. Beisner
*Attorney, Agent, or Firm*—Fish & Richardson

[57] ABSTRACT

A biological cell sorter, comprising: a first laser for emitting a first laser beam directed to a point in a tube conducting biological cells in a single file, a first light detector for detecting a cell to be destroyed according to a light emitted from the cell as a result of impinging the first laser beam upon the cell and producing a trigger signal when a cell to be destroyed is detected; a second laser for emitting a second laser beam directed to another point in said guide path downstream of the mentioned point when the trigger signal is supplied thereto; a delay circuit for delaying activation of the second laser by a delay time corresponding to a travel time which the cell requires to travel between the two points; a time measuring circuit for measuring a time interval between two succeeding trigger signals; and a correction circuit such as a look-up table for adjusting the delay time according to said time interval between the two succeeding trigger signals. Thus, even when the response time of the second laser beam is affected by the frequency of second laser beam emission, it is possible to destroy the cells to be destroyed with an extremely high precision. Owing to the high precision achieved by the present invention, the second laser beam can be accurately directed to the intended cells, and the power efficiency of the second laser can be improved.

6 Claims, 6 Drawing Sheets

BIOLOGICAL CELL SORTER

TECHNICAL FIELD

The present invention relates to a biological cell sorter for sorting out and killing or destroying unnecessary biological cells.

BACKGROUND OF THE INVENTION

It has been proposed to sort out unnecessary biological cells by sorting them out and radiating a laser beam thereon with an extremely high precision.

Referring to FIGS. 6 and 7 which show a basic principle of such a biological cell sorter, biological cells C are conducted as an extremely fine flow as indicated by the arrow in FIG. 6, and a detection laser beam L1 produced by a detection laser 33 is impinged upon this flow of biological cells C at a point A via a condenser lens 34. The light L2 dispersed by the cells C or the fluorescent light produced from the cells C as a result of laser radiation is received by a light detector 38 via a condenser lens 36, and is then converted into an electric pulse signal "d" (refer to FIG. 7(a)).

The pulse signal d is supplied to a determination circuit 39 so as to be determined if there is any unnecessary cell to be found in the flow of cells, and when any unnecessary cell is detected supplies a destroy command pulse "e" (FIG. 7(b)) to a delay circuit 41. The delay circuit 41 activates a pulse laser 40 for cell destruction into emitting a pulse laser beam L3 towards the cell to be destroyed at a point B after a certain time delay "t" by sending a pulse "h" (refer to FIG. 7(c)) to the pulse laser 40. This time delay "t" corresponds to the time interval required for the cell flow to travel from the point A to the point B. Thus, the pulse laser 40 destroys the cells which are determined to be unnecessary by the detection circuit 39 and lets pass the cells which are found to be necessary by the determination circuit 39.

However, in reality, there is a certain time lag after the pulse "h" is sent to the pulse laser 40 and a pulse laser beam L3 is actually produced from the destruction laser 40, and should this time lag fluctuate the pulse laser 40 may not be able to destroy intended cells. As a matter of fact, when a solid state laser such as continuous YAG laser is used in combination with a so-called Q switch which makes use of an acoustooptical device for converting laser into a pulse beam, the delay time "td" between the arrival of the pulse "h" and the emission of the laser beam L1 tends to change in dependency upon the frequency of pulse laser emission. Normally, the delay time "td" increases with an increase in the frequency of pulse laser emission. In other words, the more recent the previous laser beam emission was, the longer it takes for the pulse laser to emit the next laser beam. This problem is more pronounced when the duration of the pulse laser beam is short in comparison with the delay times t and td, and when the intensity of the pulse laser beam L3 is so low that it must be focused upon an extremely small point.

BRIEF SUMMARY OF THE INVENTION

In view of such recognition and other considerations, a primary object of the present invention is to provide a biological cell sorter which can accurately destroy unnecessary cells.

A second object of the present invention is to provide a biological cell sorter which can achieve a high sorting accuracy with a relatively simple and economical structure.

A third object of the present invention is to provide a biological sorter whose accuracy is not affected by a large variation in the frequency of pulse laser emission.

These and other objects of the present invention can be accomplished by providing a biological cell sorter, comprising: guide means for moving biological cells along a guide path substantially at a constant speed; a first laser beam emitter for emitting a first laser beam directed to a first point in said guide path; a first light detector for detecting a cell to be destroyed according to a light emitted from said cell as a result of impinging said first laser beam upon said cell and producing a trigger signal when a cell to be destroyed is detected; a second laser beam emitter for emitting a second laser beam directed to a second point in said guide path which is located downstream of said first point when said trigger signal is supplied thereto; delay means interposed between said first light detector and said second laser beam emitter for delaying activation of said second laser beam emitter by said trigger signal by a delay time corresponding to a travel time which said cell requires to travel from said first point to said second point; means for measuring a time interval between current trigger signal and a preceding trigger signal; and correction means for adjusting said delay time according to said time interval between said two succeeding trigger signals.

Thus, the present invention is provided with means for detecting the intervals of pulse laser beam emission, and means for correcting the delay time of emitting the pulse laser beam from the time of detection of each unnecessary cell. Therefore, even when the response time of the pulse laser is affected by the frequency of pulse laser beam emission, it is possible to destroy unneccessary cells with an extremely high precision.

According to a preferred embodiment of the present invention, said first light detector is provided with a electronic table for correcting said delay time according to said detected time interval between two succeeding trigger signals, and said first light detector is provided on another side of said first laser beam emitter with respect to said guide path, and is provided with a beam stopper to prevent said first laser beam from being directly projected upon said first light detector and/or laterally from said guide path defining a substantially right angle with respect to the central axial line of said first laser beam.

Optionally, a second light detector for receiving light produced from said cell as a result of impinging said second light beam upon said cell may be provided so as to permit monitoring destruction of said cell by said second laser beam.

BRIEF DESCRIPTION OF THE DRAWINGS

Now the present invention is described in the following in terms of a specific embodiment with reference to the appended drawings, in which.

DETAILED DESCRIPTION OF THE PREFERRED EMBODIMENTS

Figure 2:
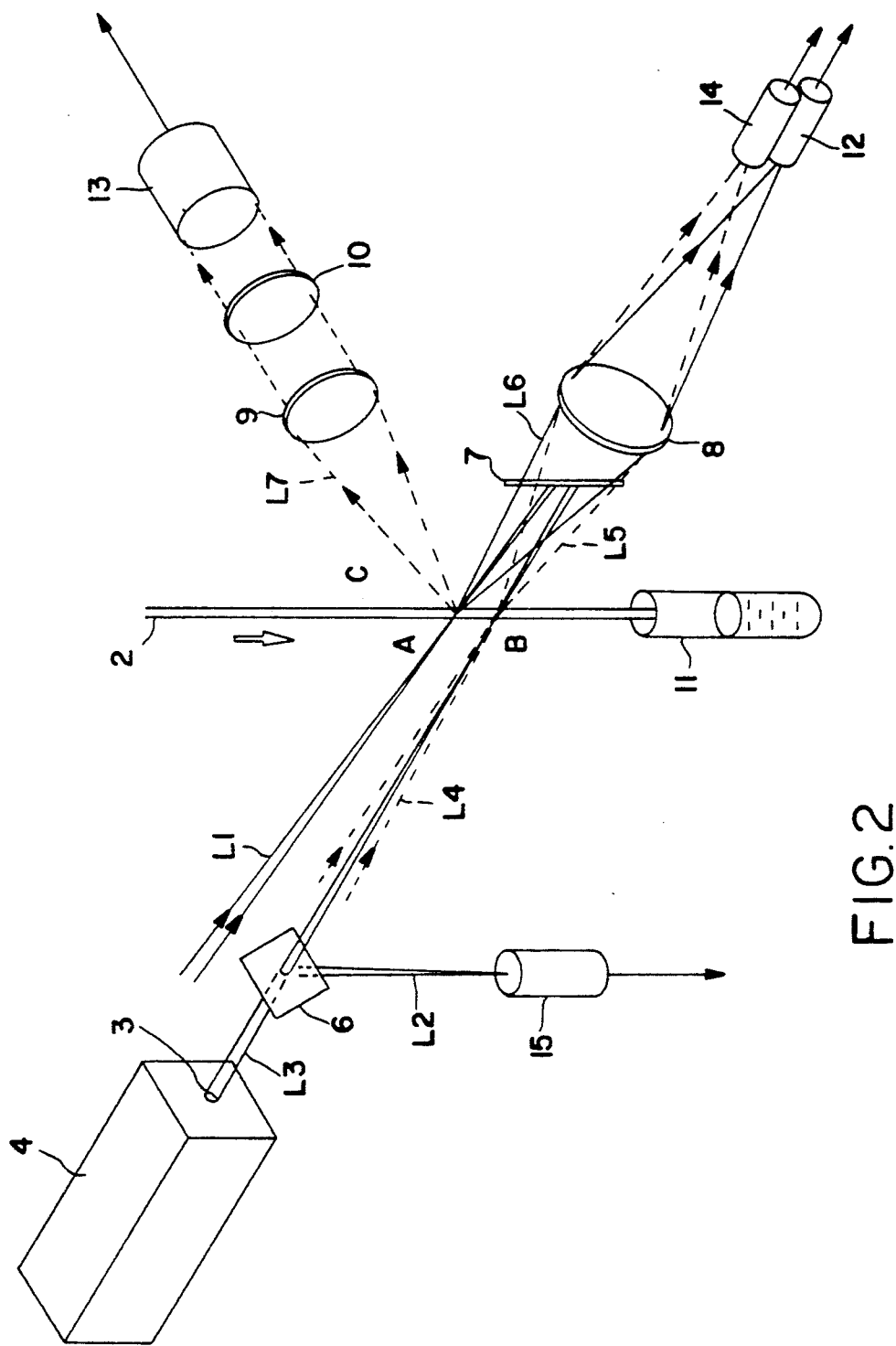
FIG. 2 is a diagram illustrating the optical arrangement of the preferred embodiment.

Referring to FIG. 2 showing the optical system of an embodiment of the biological cell sorter according to the present invention. Biological cells are conducted through a extremely fine transparent tube as a cell flow 2, and the cells in this tube flow along the center line of the tube in a single file by the effect of fluid dynamic focusing. At the downstream end of this tube is provided a reservoir 11 for receiving biological cells which have been sorted. A detection laser beam L1 produced from a detection laser 3 is impinged upon a point A (detection point) of the cell flow 2. The detection laser 3 may consist of a continuous laser such as a He—Ne laser, Ar laser, Kr laser, He—Cd laser, semiconductor lasers and so on.

The forward dispersion light L6 produced from the cells C at the point A is focused by a condenser lens 8 upon a light detector 12. The light directly issuing from the detection laser 3 is shielded by a beam stopper 7 placed in the direct path of light from the detection laser 3 to the light detector 12.

The lateral dispersion light L7 and fluorescent light produced from the cells C at the point A and directed in a laterally perpendicular direction is focused by a condenser lens 9 upon a light detector 13 via a color filter 10.

Numeral 4 denotes a pulse laser such as an Nd:YAG semiconductor laser and other high frequency lasers for destroying biological cells. In particular, purple light having a wave length less than 300 nm is desirable because it can be absorbed by cells even when they are not dyed. The pulse laser beam L3 from this pulse laser 4 is impinged upon a point B (sorting point) which is slightly downstream of the point A. A part of the pulse laser beam L2 from the pulse laser 4 is divided from the main beam by a beam splitter 6 and is directed to a pulse laser beam detector 15.

A laser beam L4 is used for monitoring the positions of biological cells in order to adjust the timing of emission of the pulse laser beam L3. This laser beam L4 may be produced from a continuous laser 5 (refer to FIG. 1), but may also be obtained by dividing a part of the detection laser beam L1 with a beam splitter. This position monitoring laser beam L4 has a same central axial line as the pulse laser beam L3, and is accordingly impinged upon the point B. A monitor light L5 which is produced as a result of impinging the laser beam L4 upon the cells at the point B is received by a monitoring light detector 14. The aforementioned beam stopper 7 also stops the laser beam L4 from being directly impinged upon the monitoring light detector 14.

Now the circuit structure of this biological cell sorter is described in the following. It should be understood that the arrangement of the various parts of the biological sorter is selected for the convenience of illustration and description, and does not necessarily represent the actual arrangement.

Figure 1:
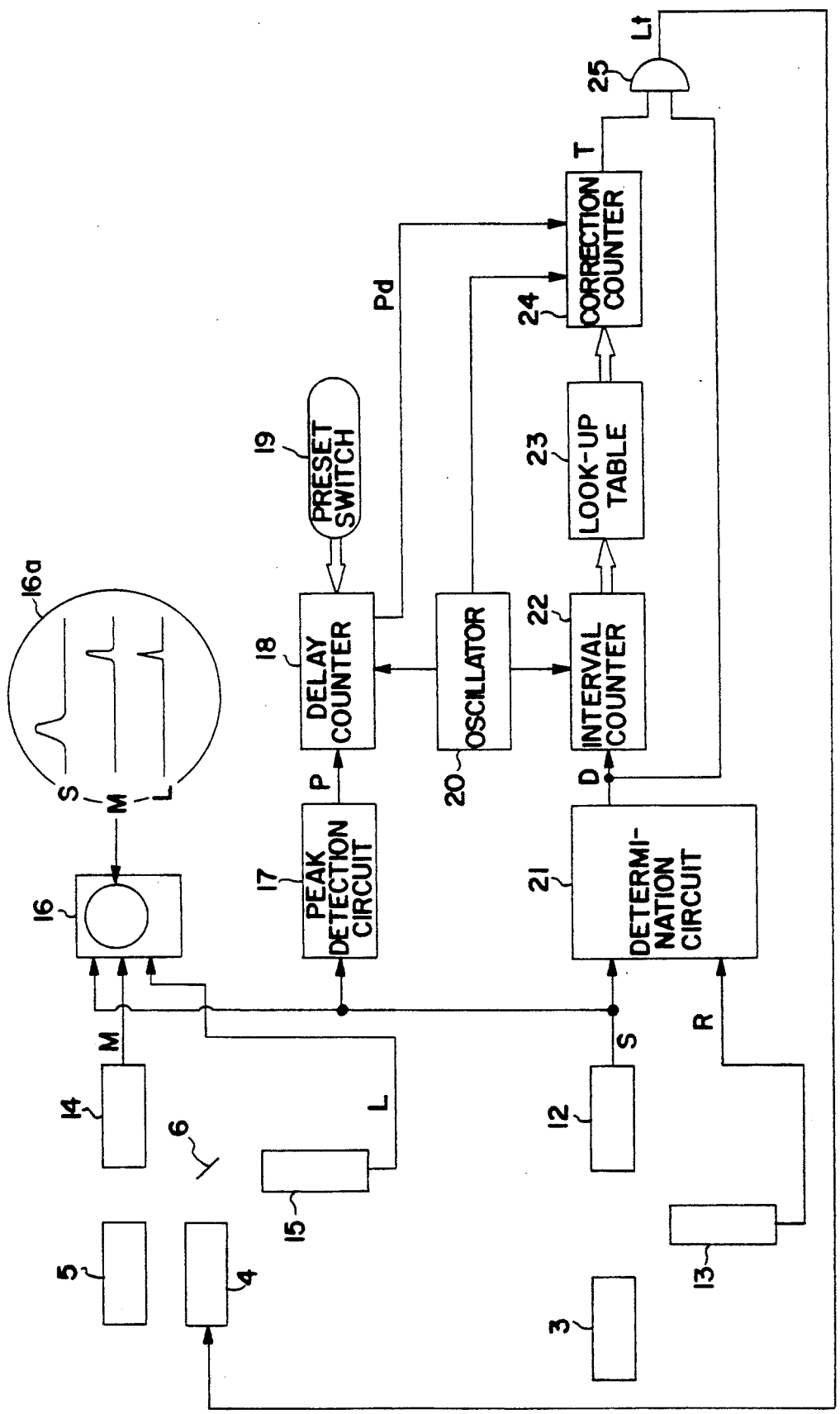
FIG. 1 is a block diagram of a preferred embodiment of the biological cell sorter according to the present invention.

Referring to FIG. 1, the pulse signal output "S" of the light detector 12 for the forward dispersed light is supplied to an oscilloscope 16 for displaying various wave forms, a peak detection circuit 17 for detecting that a cell has passed through the center of the detection laser beam L1, and a determination circuit 21 for determining whether the cell is need to be destroyed or not.

Figure 4:
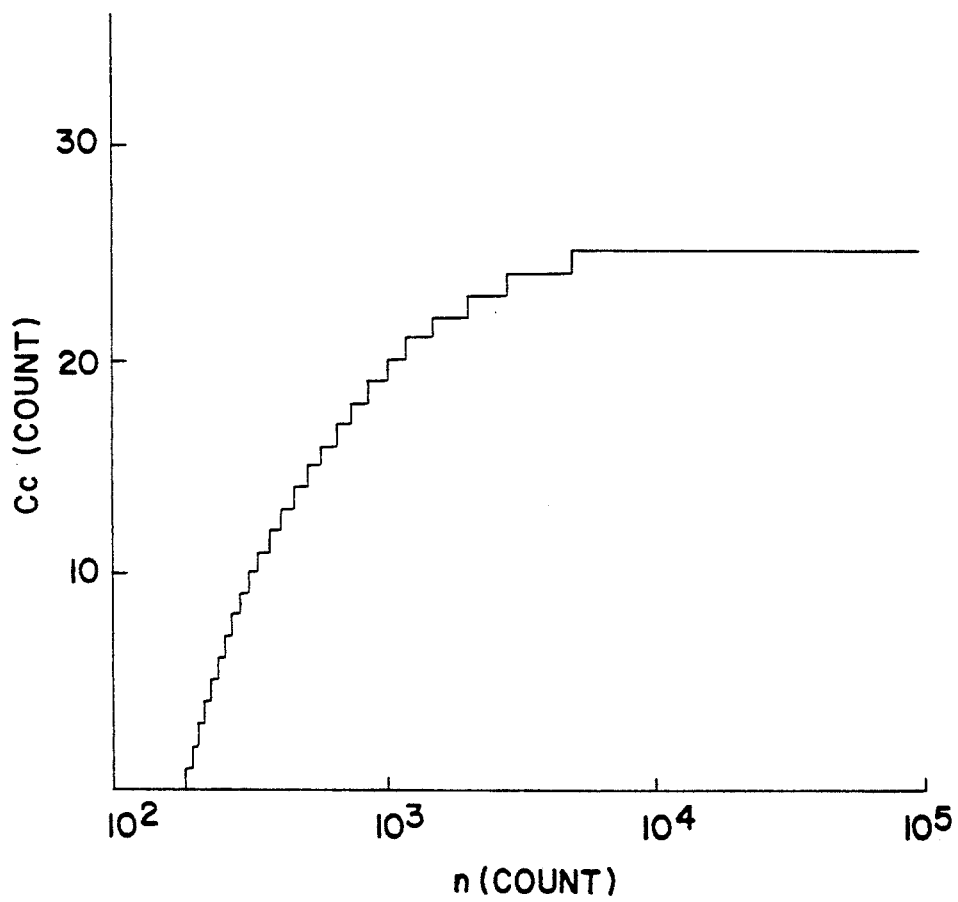
FIG. 4 is a graph representing the contents of the look-up table.

The determination circuit 21 receives a signal "R" from the lateral dispersion light detector 13 as well as the pulse signal "S" from the front dispersion light detector 13 to determine if each of the cells flowing past the point A is needed or not, and sends a determination pulse "D" to an interval counter 22 and and AND circuit 25 every time an unnecessary cell or a cell to be destroyed is detected. The count of the interval counter 22 counts the clock pulses from an oscillator 20 during the time interval extending from the leading edge of the previous determination pulse to the leading edge of the current determination pulse. The count of the interval counter 22 is supplied to a look-up table 23. The look-up table 23 in turn supplies a correction count, which is decided according to the time interval between the leading edges of the most recent two succeeding pulses, to a correction counter 24. Contents of an exemplary look-up table 23 are given in FIG. 4. In this case, the clock frequency of the oscillator 20 is 10 MHz, and the horizontal axis of the graph of FIG. 4 represent the count n of the interval counter 22 and the vertical axis of this graph represents the correction count Cc. In this embodiment, ROM is used for the look-up table 23, but it may also consist of RAM into which the data is written every time the system is started up.

An output "P" from the peak detection circuit 17 is supplied to a delay counter 18. The delay time during which the delay counter 18 is activated is adjusted by using a preset switch 19 so as to be substantially equal to the time interval which a cell requires to travel from the point A to the point B less the time interval from the time point a trigger pulse Lt is supplied to the pulse laser 4 to the time point the pulse laser beam L3 is actually generated. In this way, the delay counter 18 counts down in synchronism with the clock pulses from the oscillator 20 from the time point at which a pulse signal "P" from the peak detection circuit 17 is received, and produces a delay pulse Pd when the count is reduced to zero. This delay pulse Pd is supplied to the correction counter 24 which, then, starts counting down from a count Cc set up in the look-up table in synchronism with the clock pulses of the oscillator 20, and produces a timing pulse "T" when the count is reduced to zero.

This timing pulse "T" is supplied to the aforementioned AND circuit 25 which produces a laser trigger pulse Lt as a logical sum of the determination pulse "D" of the determination circuit 21 and the timing pulse "T". The pulse laser 3 for cell destruction emits the pulse laser beam L3 in response to this laser trigger pulse Lt.

The oscilloscope 16 displays the output "S" of the front dispersion light detector 12, the output "M" of the position monitoring light detector 14, and the output "L" of the light detector 15 for the pulse laser beam. The operator adjusts the preset switch 19 so as to match the wave form of the output "L" of the light detector 15 with the wave form of the output pulses "M" of the position monitoring light detector 14 on the time axis, and ensures the pulse laser beam L3 is accurately impinged upon unnecessary biological cells.

Now the operation of this cell sorter is described in the following with reference to the time chart of FIG. 3.

When a cell arrives at the point A, the cell produces a front dispersion light L6 and a lateral dispersion light L7, and the light detectors 12 and 13 accordingly produce output signals S1 and R1. The signals S1 and R1 are supplied to the determination circuit 21 which then carries out necessary arithmetic operations. Meanwhile, the signal S1 is also supplied to the peak detection circuit 17, and, upon detection of a peak in the signal S1, produces a peak signal P1.

Figure 3:
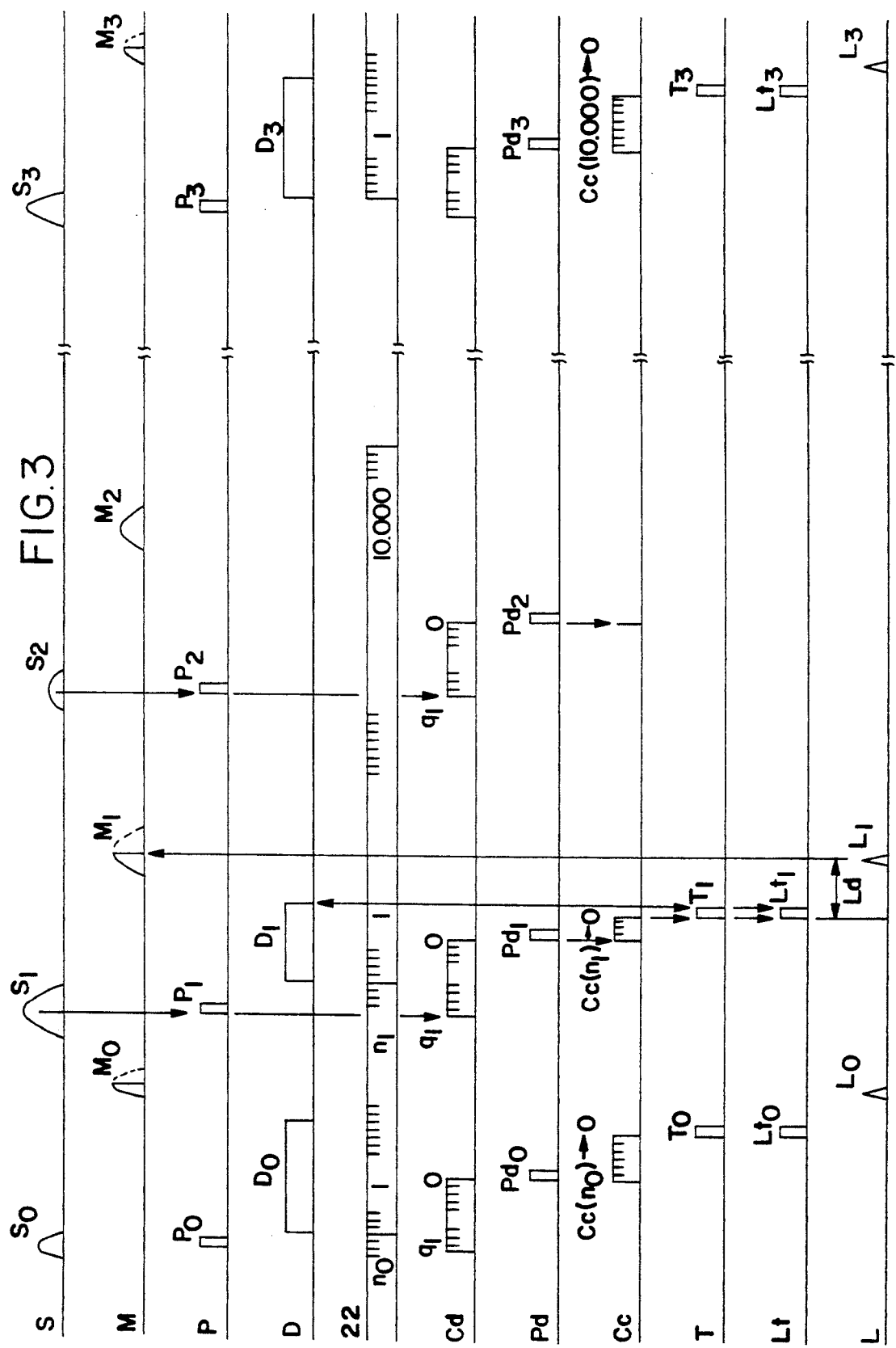
FIG. 3 is a time chart for describing the operation of the preferred embodiment.

The peak signal P1 is supplied to the delay counter 18 which counts down in synchronism with the clock pulses of the oscillator 20 (Cd in FIG. 3). The initial value "q" of this delay counter 18 is adjusted by the preset switch 19. The delay counter 18 produces a delay pulse Pd1 when its count is reduced to zero.

Meanwhile, after elapsing of the time required for carrying out the arithmetic operations in the determination circuit 21, a determination pulse D1 rises up. This triggers an input of the count n1 of the interval counter 22 to the look-up table 23, and, at the same time, resets the interval counter 22 so as to count from 1 all over again. The look-up table 23 supplies a count Cc(n1) corresponding to n1 according to the relationship given in FIG. 4. Upon receiving the delay pulse Pd1, the correction counter 24 starts counting down from the count Cc(n1), and produces the timing pulse T1 when its count is reduced to zero. Then, the AND circuit 25, as it receives both the timing pulse T1 and the determination pulse D1, produces the laser trigger pulse Lt as a logical sum thereof. The laser trigger pulse Lt is supplied to the pulse laser 4 which then emits the laser pulse beam L3 after a delay time Ld1. This pulse laser beam L3 is detected by the light detector 15, and its wave form can be monitored on the oscilloscope 16. The determination pulse D1 falls in level simultaneously as the rise of the timing pulse T1.

In FIG. 3, if a necessary cell is detected by a signal S2, no determination pulse is generated, and the interval counter 22 continues to count down. Then, as the table is not looked up, the correction counter 24 is kept in its zero condition from the previous count down operation, and produces no timing pulse.

Figure 5:
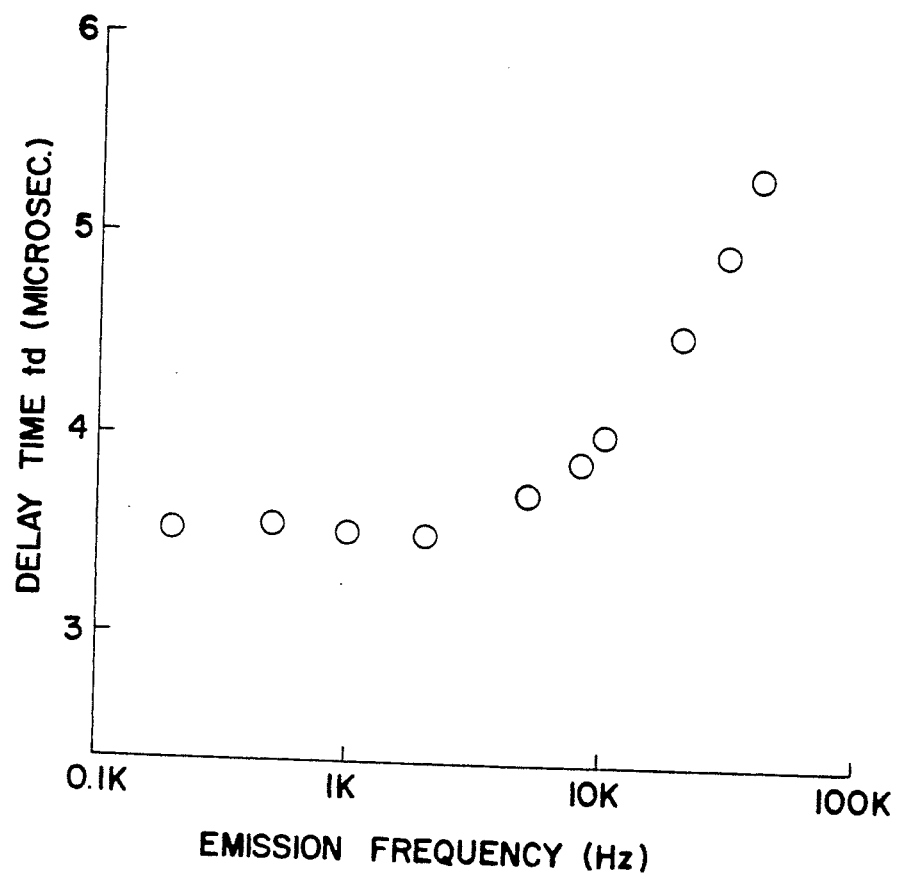
FIG. 5 is a graph showing the relationship between the frequency of pulse laser beam emission and the response time of the pulse laser.
Figure 6:
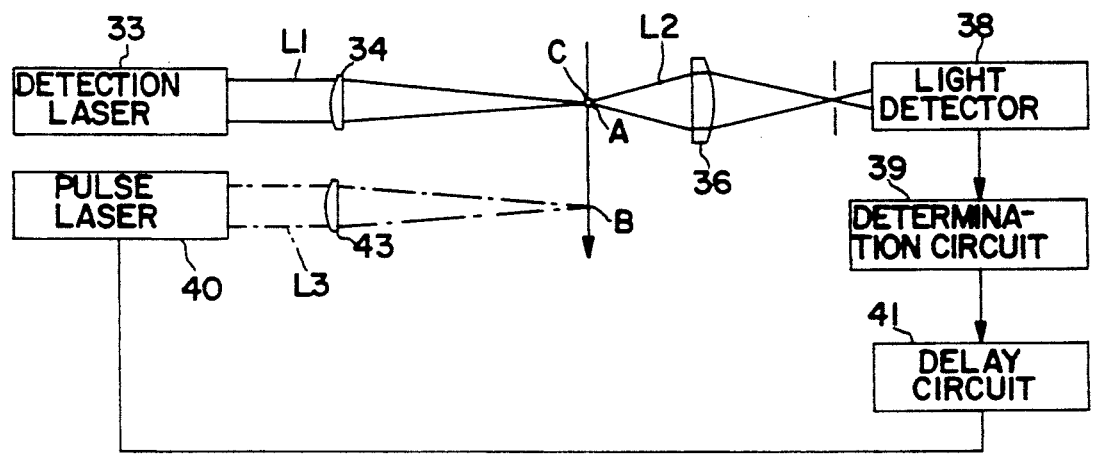
FIG. 6 is a block diagram illustrating the working principle of the biological cell sorter.
Figure 7:
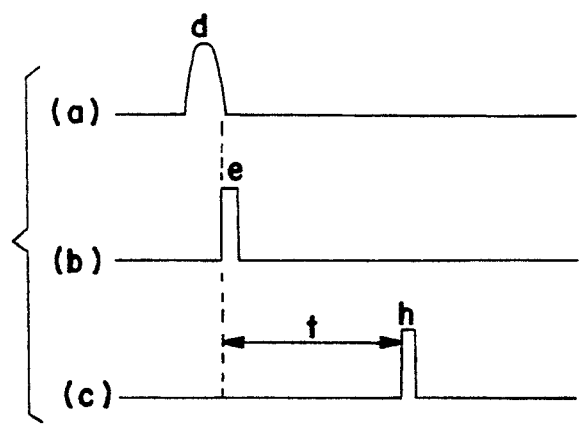
FIG. 7 is wave form diagrams for describing the operation of the biological cell sorter.

If the interval of the two succeeding signal outputs from the front dispersion light detector is long, for instance 500 microseconds or more, or, in other words, a condition represented by the horizontal part of the laser beam emission frequency versus delay time graph of FIG. 5 is produced, the interval counter 22 does not count beyond 10,000.

The parts of the pulses M0, M1 and M3 of the output signal "M" from the position monitoring light detector 14 indicated by broken lines (the right hand sides of the pulses) mean that the cells were destroyed by the pulse laser beam L3. Thus, the oscilloscope 16 allows the monitoring of the destruction of unnecessary cells.

In this embodiment, the output signal of the front dispersion light detector 12 was supplied to the peak detection circuit 17, but it is also possible to supply thereto the output signal of the lateral dispersion light detector 13 instead.

Thus, the present invention is provided with means for detecting the intervals of pulse laser beam emission, and means for correcting the delay time of emitting the pulse laser beam from the time of detection of each unnecessary cell. Therefore, even when the response time of the pulse laser is affected by the frequency of pulse laser beam emission, it is possible to destroy unnecessary cells with an extremely high precision. Owing to the high precision achieved by the present invention, the pulse laser beam is accurately directed to the unnecessary cells, and the power efficiency of the pulse laser can be improved. Therefore, the overall cost and size of the biological cell sorter can be significantly reduced.

What we claim is:

1. A biological cell sorter, comprising:
   guide means for moving biological cells along a guide path substantially at a constant speed;
   a first laser beam emitter for emitting a first laser beam directed to a first point in said guide path;
   a first light detector for detecting a cell to be destroyed according to a light emitted from said cell as a result of impinging said first laser beam upon said cell and producing a trigger signal when a cell to be destroyed is detected;
   a second laser beam emitter for emitting a second laser beam directed to a second point in said guide path which is located downstream of said first point when said trigger signal is supplied thereto;
   delay means interposed between said first light detector and said second laser beam emitter for delaying activation of said second laser beam emitter by said trigger signal by a delay time corresponding to a travel time which said cell requires to travel from said first point to said second point;
   means for measuring a time interval between current trigger signal and a preceding trigger signal; and
   correction means for adjusting said delay time according to said time interval between said two succeeding trigger signals.

2. A biological cell sorter according to claim 1, wherein said first light detector is provided with a electronic table for correcting said delay time according to said detected time interval between two succeeding trigger signals.

3. A biological cell sorter according to claim 1, further comprising a second light detector for receiving light produced from said cell as a result of impinging said second light beam upon said cell and monitoring destruction of said cell by said second laser beam.

4. A biological cell sorter according to claim 3, wherein said second light detector is provided on another side of said second laser beam emitter with respect to said guide path, and is provided with a beam stopper to prevent said second laser beam from being directly projected upon said second light detector.

5. A biological cell sorter according to claim 1, wherein said first light detector is provided on another side of said first laser beam emitter with respect to said guide path, and is provided with a beam stopper to prevent said first laser beam from being directly projected upon said first light detector.

6. A biological cell sorter according to claim 1, wherein said first light detector is provided laterally from said guide path defining a substantially right angle with respect to the central axial line of said first laser beam.

* * * * *